US005690947A

United States Patent [19]
Habif et al.

[11] Patent Number: 5,690,947
[45] Date of Patent: Nov. 25, 1997

[54] BORAGE SEED OIL AS AN ANTI-IRRITANT IN COMPOSITIONS CONTAINING HYDROXY ACIDS OR RETINOIDS

[75] Inventors: Stephan Samuel Habif, Demarest, N.J.; John Brian Bartolone, Bridgeport, Conn.; Dennis Brian Sinfield, Highland Lakes; Falguni Snehal Nanavaty, Lawrenceville, both of N.J.

[73] Assignee: Chesebrough-Pond's USA Co., Division of Conopco, Inc., Greenwich, Conn.

[21] Appl. No.: 706,009

[22] Filed: Aug. 30, 1996

[51] Int. Cl.$^6$ ................................................ A61K 7/40
[52] U.S. Cl. .............. 424/401; 424/59; 424/69; 514/772; 514/844
[58] Field of Search .................. 424/69, 47, 59, 424/401, 49; 514/772, 844, 59

[56] References Cited

U.S. PATENT DOCUMENTS

| | | | |
|---|---|---|---|
| 5,039,513 | 8/1991 | Chatterjee | 424/47 |
| 5,082,661 | 1/1992 | Melnik | 424/401 |
| 5,252,604 | 10/1993 | Nagy et al. | 514/559 |
| 5,310,556 | 5/1994 | Ziegler | 424/401 |
| 5,445,822 | 8/1995 | Bracco | 424/401 |
| 5,476,661 | 12/1995 | Pillai et al. | 424/401 |
| 5,516,793 | 5/1996 | Duffy | 514/474 |
| 5,587,149 | 12/1996 | Punto | 424/59 |

FOREIGN PATENT DOCUMENTS

| | | |
|---|---|---|
| 0173478 | 3/1986 | European Pat. Off. . |
| 0416855 | 9/1989 | European Pat. Off. . |
| 0631662 | 1/1995 | European Pat. Off. . |
| 90/07331 | 7/1990 | WIPO . |

OTHER PUBLICATIONS

Derwent Abstract of FR 2704390 dated Nov. 4, 1994.
Derwent Abstract of FR 2604624 dated Apr. 8, 1988.
Derwent Abstract of GB 2271928 dated May 4, 1994.
Medline Abstract of Tollesson et al., "Transepidermal Water Loss and Water Content in the Stratum Corneum in Infantile Sebhorroeic Dermatitis", Acta Derm Venereol (Sweden), Feb. 1993, 73 (1), pp. 18–20.
Medline Abstract of Bahmer et al., "Treatment of Atopic Dermatitis with Borage Seed Oil (Glandol)—A Time Series Analytic Study", Kinderarztl Prax (Germany), Oct. 1992, 60 (7), pp. 199–202.
Ingredient Label 1: A composition marketed more than 1 year prior to filing of the present application.

*Primary Examiner*—Joseph L. Schofer
*Assistant Examiner*—D. Faulkner
*Attorney, Agent, or Firm*—Rimma Mitelman

[57] ABSTRACT

Compositions containing hydroxy acids and/or retinoids and further containing borage seed oil as an anti-irritant. Borage seed oil was found to be uniquely effective (when compared to gamma-linolenic acid, or other anti-irritants containing gamma-linolenic acid or other known anti-irritants) in reducing the irritation caused by hydroxy acids and/or retinoids.

7 Claims, No Drawings

BORAGE SEED OIL AS AN ANTI-IRRITANT IN COMPOSITIONS CONTAINING HYDROXY ACIDS OR RETINOIDS

FIELD OF THE INVENTION

The present invention relates to the use of borage seed oil in a composition and a method for reducing or eliminating skin irritation induced by hydroxy acids or retinoids.

BACKGROUND OF THE INVENTION

Hydroxy acids (HAs) and retinoids have been proven to deliver cosmetic benefits, such as improvement in the appearance of photodamaged or naturally aged skin, skin lightening, treatment of age spots, etc. Unfortunately, their use at high concentrations may occasionally be associated with skin irritation, e.g. skin redness and stinging sensation upon application. The irritation can be ameliorated by lowering the amount of an active ingredient in the composition or by reducing the active's penetration through the skin. A serious drawback of both approaches is that the efficacy is impaired. The HA related irritation can be reduced by raising the composition's pH but this method yields reduced efficacy through a decreased HA penetration through the skin. It is desirable to reduce or eliminate the irritation potential of HAs and/or retinoids while maintaining their efficacy.

European Patent Application 0631722 (Johnson & Johnson) discloses the use of glycolic acid to reduce irritation of the skin by retinol. U.S. Pat. No. 5,252,604 (Nagy et al.) teaches the use of tocopherols for retinoic acid induced irritation. U.S. Pat. No. 5,516,793 (Duffy) discloses the use of ascorbic acid to ameliorate the irritation caused by various topical ingredients, including HAs and retinoids.

U.S. Pat. No. 5,476,661 (Pillai et al.) discloses cosmetic compositions containing 25-hydroxycalciferol and a lipid ingredient. Numerous optional ingredients are listed among which are mentioned HAs and/or retinoids and unsaturated fatty acids, such as gamma linolenic acid (GLA). Pillai et al. do not address the problem of skin irritation, do not teach the use of any agent for reducing skin irritation and do not teach the use of borage seed oil.

European Patent Application 0416855 (Efamol) discloses treatment of skin damage due to radiotherapy with gamma linolenic acid (GLA) and also teaches a variety of suitable plant sources of GLA, including Borage species. PCT application WO 90/07331 (Went) teaches treatment of inflammation arising from arthritis or headache by topical application of GLA; borage seed is taught as a suitable source. European Patent Application 0173478 (Efamol) discloses treatment of inflammatory skin disorders with compositions containing GLA and glucocorticoids; borage species such as Borago officinalis is mentioned as a rich source of GLA. French patent 2,704,390 (Boiron) discloses an oral supplement containing borage seed oil to provide anti-aging benefits to skin. French patent 2,604,624 (Parfums Rochas) discloses skin care compositions containing polyunsaturated carboxylic acids, such as GLA; borage is said to be rich in GLA. U.S. Pat. No. 5,445,822 (Bracco) discloses cosmetic compositions containing polyunsaturated acids such as GLA.

Great Britain Patent 2,271,928 (Laing) discloses the use of borage family plant extracts for alleviation of skin disorders and irritations.

Tollesson et al., "Transepidermal Water Loss and Water Content in the Stratum Corneum in Infantile Sebhorroeic Dermatitis", Acta Derm Venereol (Sweden), Feb. 1993, 73 (1), p. 18–20, disclose the use of topically applied borage oil for treatment of sebhorroeic dermatitis.

Bahmer et al., "Treatment of Atopic Dermatitis with Borage Seed Oil (Glandol)—A Time Series Analytic Study", Kinderarztl Prax (Germany), Oct. 1992, 60 (7), p. 199–202, disclose the use of borage oil for the treatment of atopic dermatitis.

The art discussed above does not teach any compositions containing borage seed oil in combination with HAs and/or retinoids. The art does not teach the use of GLA or borage seed oil to reduce irritation associated with the use of HAs and/or retinoids. Furthermore, it was found as part of the present invention that among GLA containing plant sources borage seed oil was particularly effective at ameliorating irritation induced by HAs or retinoids and that this effect could not be attributed merely to the presence of GLA in the borage seed oil.

SUMMARY OF THE INVENTION

The present invention includes, in part, a composition containing a cosmetic benefit ingredient selected from the group consisting of hydroxy acids and certain retinoids and further containing borage seed oil in an amount effective to ameliorate the irritation induced by the active agent.

The invention also includes a method for reducing irritation induced by the topical application of a composition containing HAs or retinoids, the method comprising topically applying borage seed oil in an amount effective to reduce irritation induced by the composition. According to the inventive method, borage seed oil may be co-present with HAs and/or retinoids in the same composition, or borage seed oil may be applied from a separate composition.

According to the present invention, by virtue of topical application of borage seed oil, the irritation induced by the topical application of HAs and/or retinoids is reduced or eliminated. It has been found as part of the present invention that not all known anti-irritants, even those that contain GLA, ameliorate HA/retinoid induced irritation.

DETAILED DESCRIPTION OF THE INVENTION

Borage seed oil is an essential ingredient of the inventive compositions.

Borage seed oil is obtained from the seeds of borage plant, also known as *Borago officinalis*L. (Boraginaceae), which is an herbaceous annual plant, native to Europe, Asia Minor and North Africa, naturalized in the United States. The seed oil contains: gamma-linoleic acid (GLA), ~24%, sterols (e.g., campestrol and sitosterol), tocopherols, linoleic acid (~38%), oleic acid (14.5–23%), palmitic (~4.7%), amabiline, etc. See Whipkey, A., J. E. Simon and J. Janick, "In Vivo and In Vitro Lipid Accumulation in *Borago officinalis* L.", JAOCS, 65 (6), 979–984 (1988); and Leung, A. Y. and S. Foster, "Encyclopedia of Common Natural Ingredients Used in Food, Drugs and Cosmetics", 2nd ed., John Wiley & Sons, Inc., New York (1996).

Borage seed oil is employed according to the present invention to reduce or eliminate the skin irritation induced by hydroxy acids and/or retinoids.

The amount of borage seed oil in the inventive compositions ranges generally from about 0.05% to about 10% by weight of the composition, preferably from about 0.1% to about 5%, most preferably from about 0.5% to about 2%.

Hydroxyacids enhance proliferation and increase ceramide biosynthesis in keratinocytes, increase epidermal thickness, and increase desquamation of normal skin resulting in smoother, younger looking skin.

The hydroxy acid can be chosen from α-hydroxy acids, β-hydroxyacids (e.g. salicylic acid), other hydroxycarboxylic acids (e.g., dihydroxycarboxylic acid, hydroxydicarboxylic, hydroxytricarboxylic) and mixtures thereof or combination of their stereoisomers (DL, D or L).

Preferably the hydroxy acid (ii) is chosen from α-hydroxy acids having the general structure (13):

where M is H— or $CH_3(C_fH_g)_h$—, f is an integer of from 1 to 27, g is an integer of from 2 to 54, and h is 0 or 1.

Even more preferably the hydroxy acid is chosen from lactic acid, 2-hydroxyoctanoic acid, hydroxylauric lactic acid, glycolic acid, and mixtures thereof. When stereo isomers exist, L-isomer is most preferred.

The keto acids can be chosen from α-keto acids, β-keto acids and mixtures thereof.

A particularly preferred α-keto acid is 2-keto octanoic acid.

It is to be understood that depending on the pH of the composition, the hydroxy acid may be present as a salt, e.g. ammonium or potassium or sodium salt.

Although the inventive compositions may have any pH in the general range of 2.5 to 10, the inventive compositions are particularly useful when they are at an acidic pH (especially if they contain a hydroxy acid), most preferably at a pH of 3–4, because such compositions are particularly irritating.

Retinoids enhance keratinocyte proliferation in vitro, increase epidermal thickness and increase collagen synthesis by dermal fibroblasts. This results in protection from sun damage and smoothing of wrinkled skin. The term "retinoids" as used herein includes retinoic acid, retinol, retinal and $C_2$–$C_5$ retinyl esters. Included in the term "retinoic acid" are 13-cis retinoic acid and all-trans retinoic acid.

The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_2$–$C_5$ esters of retinol, preferably $C_2$ and $C_3$ esters, and most preferably $C_2$ ester because it is more commonly available. Retinyl esters included in the invention are also known as: retinyl acetate, retinyl propionate, retinyl butyrate, and retinyl pentanolate.

A particular advantage of the inventive compositions is that higher amounts of hydroxy acids or retinoids may be employed without causing skin irritation. Preferably the amount of the hydroxy acid component present in the composition according to the invention is from 0.01 to 20%, more preferably from 2 to 12% and most preferably from 4 to 12% by weight.

A retinoid may be present in the inventive compositions in an amount 33 to 330,000 IU per gram of the composition, preferably 330 to 16,500 IU, most preferably 1,650 to 6,600 IU. Again, a higher amount of a retinoid may be employed in the inventive compositions without causing skin irritation, due to the co-presence of borage seed oil.

Most preferred inventive compositions containing borage seed oil anti-irritant include retinol and/or glycolic acid and/or lactic acid because these ingredients have been found to cause irritation yet they were found to be particularly efficacious at delivering cosmetic benefits.

The skin treatment composition of the invention also includes a cosmetically acceptable vehicle or a carrier which is inert, usually an ingredient present in the highest amounts, and functioning to deliver active or performance ingredients. Vehicles other than water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition. The amount of vehicle may range from about 2 to about 99 wt %, preferably from about 50 to about 99%, most preferably from about 80 to 99%, by weight of the total composition.

Optional Skin Benefit Materials and Cosmetic Adjuncts

Various types of active ingredients may be present in cosmetic compositions of the present invention. Actives are defined as skin benefit agents other than emollients and other than ingredients that merely improve the physical characteristics of the composition. Although not limited to this category, general examples include anti-wrinkle compounds and sunscreens and tanning agents.

Sunscreens include those materials commonly employed to block ultraviolet light. Illustrative compounds are titanium dioxide, the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

According to the present inventive method, the skin irritation induced by the active ingredient is reduced or eliminated by topical application of borage seed oil. The borage seed oil may be co-present with the active, or it may be applied to the skin separately from the active.

Product Form and Packaging

The topical skin treatment composition of the invention can be formulated as a lotion, a fluid cream, a cream or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The borage seed oil may be packaged separately from the composition containing HAs and/or retinoids.

The following specific examples further illustrate the invention, but the invention is not limited thereto. Borage seed oil employed in the examples was obtained from Canamino, Inc. (Northport, N.Y.).

EXAMPLE 1

Seventeen subjects were tested according to Irritation Test Method described below.

Irritation Test Method Four Exposure Patch Test: The objective was to compare the level of irritation produced by various test materials after repeated patch applications. The test materials were held in contact with the skin under occlusive conditions. The outer upper arm of the panelist was designated as the area of application. Bandage type dressing (Scanpor® tape) was used to hold the patches (25 mm Hill Top® Chamber fitted with 18 mm diameter disc of Webril® padding) into place. Both upper arms of the panelist were used. Patches were applied in a balanced random order.

Patches were applied at 9:00 o'clock Monday morning and removed at 9:00 o'clock Tuesday morning (24 hour exposure). A new set of patches was applied at 3:00 o'clock Tuesday afternoon and removed Wednesday morning at 9:00 o'clock (18 hour exposure). A third set of patches was applied at 3:00 o'clock Wednesday afternoon and removed Thursday morning at 9:00 o'clock (18 hour exposure). A final set of patches was applied at 3:00 o'clock Thursday afternoon and removed Friday morning at 9:00 o'clock (18 hour exposure).

Each time the patches were removed, the sites were rinsed with warm water and patted dry. The test sites were then marked with a surgical skin marking pen to ensure location for grading and subsequent patch applications. Test sites were evaluated at 3:00 p.m. on Tuesday, Wednesday, Thursday and Friday of the study, prior to re-patching.

Skin irritation such as moderate redness, dryness, and/or itching of the test site is expected. Swelling of the test sites is possible. If any test has moderate redness or any swelling at evaluation, that particular test site should not be repatched.

The test sites on each arm were visually ranked by two trained examiners under consistent lighting. The test sites were ranked in order of severity. The examiner ranking responses at the first evaluation period continued ranking the sites each day throughout the study.

In ranking the reactions, the site with the most severe response was given the lowest score. The site with the second most severe response was given the second lowest score, etc. There was no forced ranking. If two or more sites had no response or the same response (no difference between sites), an average of the ranks was assigned. If a site has been discontinued, due to degree of irritation the site retained the rank it received at the time dosing was discontinued.

Statistical Analysis

The ranking results from the patch treatments were statistically compared by nonparametric statistical methods. The test materials containing the anti-irritants were compared to the corresponding control containing only hydroxy acid and/or retinoid, using Friedman's Rank Sum. Treatments were compared to the Formula 2 (control) at each evaluation point using Friedman's analysis with the panelist acting as a block (i.e., each panelist was tested with each test treatment). p-value of $\leq 0.1$ was considered statistically significant.

An emulsion base was prepared having the following formula.

| EMULSION BASE FORMULA | | |
|---|---|---|
| FULL CHEMICAL NAME OR CFTA NAME | TRADE NAME AND % ACTIVE AS RECEIVED | WT. % |
| water, DI | | 46.54 |
| disodium EDTA | Sequesterene Na2 | 0.05 |
| magnesium aluminum silicate | Veegum Ultra | 0.6 |
| methyl paraben | Methyl Paraben | 0.15 |
| simethicone | DC Antifoam Emulsion | 0.01 |
| butylene glycol 1,3 | Butylene Glycol 1,3 | 3.0 |
| hydroxyethylcellulose | Natrosol 250HHR | 0.5 |
| glycerine, USP | Glycerine USP | 2.0 |
| xanthan gum | Keltrol 1000 | 0.2 |
| triethanolamine | Triethanolamine 99(%) | 1.2 |
| stearic acid | Pristerene 4911 | 3.0 |
| propyl paraben NF | Propylparaben NF | 0.1 |
| glyceryl hydrostearate | Naturechem GMHS | 1.5 |
| stearyl alcohol | Lanette 18DEO | 1.5 |
| isostearyl palmitate | Protachem ISP | 6.0 |
| C12–15 alcohols octanoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | MYRJ 59 | 2.0 |
| water, DI | | q.s. to 99.80 |
| alpha-bisabolol | Alpha-bisabolol | 0.2 |
| pH | | 7–8 |

Compositions 1–5 containing ingredients as indicated in Table 1 were tested using the Irritation Test Method. The results that were obtained are summarized in Table 1. The higher the Sum of Ranks, the less severe the irritation.

TABLE 1

Irritation Test Results

| COMPOSITION | INGREDIENTS | SUM OF RANKS (DAY 4) | % GLA |
|---|---|---|---|
| 1 | Base Formula | 68.5* | |
| 2 | Control: Base Formula + 8% Glycolic Acid and 0.075% Retinol | 46.5 | |
| 3 | Composition #2 + 0.5% Borage Seed Oil | 69.5* | 0.115 |
| 4 | Composition #2 + 3% Black Currant Seed Oil | 58.0 | 0.51 |
| 5 | Composition #2 + 1% Sambucus | 44.5 | |

*Significantly less irritating than composition #2.

It can be seen from the results in Table 1 that after four exposures, 8% glycolic acid with 0.075% retinol (#2) was significantly more irritating than Base formula #1. 8% glycolic acid and 0.075% retinol was also significantly more irritating than the same composition containing Borage seed oil (#3).

By contrast, 1% Sambucus (#5) or 3% Black Currant Seed Oil (#4) did not significantly reduce the irritation.

Sambucus and Black currant seed oil are known anti-irritants. Black currant seed oil also contains 17% GLA. However, neither agent was effective in reducing alpha hydroxy acid/retinol induced irritation.

The art teaches that the formulation with higher total % GLA would be expected to be less irritating. In this case, the black currant seed oil formulation would have been expected to be less irritating than the borage seed oil formulation. Surprisingly, we found that the borage seed oil formulation which contained a significantly lower concentration of GLA was less irritating than the black currant seed oil formulation, although the black currant seed oil formulation contained five times more GLA than borage seed oil.

COMPARATIVE EXAMPLE 2

Compositions 1, 2 and 6–9 containing ingredients as indicated in Table 2 were tested using the Irritation Test Method described in Example 1. Seventeen subjects were tested. The results that were obtained are summarized in Table 2. The higher the sum of ranks, the less is the irritation.

TABLE 2

Irritation Test Results

| COMPOSITION # | INGREDIENTS | SUM OF RANKS (DAY 4) |
|---|---|---|
| 1 | Base Formula | 74.5* |
| 2 | Base Formula + 8% Glycolic + 0.075% Retinol | 61.5 |
| 6 | Composition #2 + 1% Green Tea | 51.0 |
| 7 | Composition #2 + 0.1% K2 Glycyrrohetinic Acid | 54.5 |
| 8 | Composition #2 + 3% Quench T* | 58.5 |
| 9 | Composition #2 + 3% Polyol Prepolymer -2** | 57.0 |

*Statistically less irritating than composition #2.
*An anti-irritant from Centerchem (containing water, butylene glycol, kola bean extract, guarana extract, and mate extract).
**An anti-irritant from Penederm, Inc. (CFTA name PPG-12/SMDI).

It can be seen from the results in Table 2 that none of the anti-irritants tested (none contained GLA) were able to significantly reduce the irritation induced by composition #2 (containing 8% Glycolic Acid and 0.075% Retinol).

EXAMPLE 3

Compositions 10–13 containing ingredients as indicated in Table 3 were tested using the Irritation Test Method described in Example 1. Composition 10 was similar to composition 1 in Example 1, except that composition 10 additionally contained 0.5% sodium stearyl lactylate, 0.1% retinyl palmitate and 0.1% hydroxy caprylic acid ("Base Formula A"). The higher the Sum of Ranks, the less severe the irritation.

TABLE 3

Irritation Test Results

| COMPOSITION # | INGREDIENT | SUM OF RANKS (DAY 4) | % GLA IN COMPOSITION |
|---|---|---|---|
| 10 | Base Formula A | 75.5* | 0 |
| 11 | Base Formula A + 8% Glycolic Acid | 48.5 | 0 |
| 12 | Base Formula A + 8% Glycolic Acid + 0.125% GLA | 44.5 | 0.125 |
| 13 | Base Formula A + 8% Glycolic Acid + 0.5% Borage Seed oil | 61.0 | 0.115 |

*Statistically significant compared to composition #11.

It can be seen from the results in Table 3, that the addition of 8% glycolic acid (composition #11) significantly increased the irritation. Upon further addition of borage seed oil (composition #13), the irritation was directionally reduced. By contrast, a composition which contained a similar amount of GLA as composition #13, but not from borage seed oil, did not at all reduce the irritation induced by glycolic acid. This again demonstrates that borage seed oil efficacy at reducing HA irritation is unique and cannot be attributed solely to the presence of GLA.

EXAMPLE 4

Twenty-one (21) subjects were tested according to the Irritation Test Method described in example 1.

Compositions 11, 13 and 14 containing ingredients as indicated in Table 4 were tested using the Irritation Test Method. The results that were obtained are summarized in Table 4. The higher the Sum of Ranks, the less severe the irritation.

TABLE 4

Irritation Test Results

| COMPOSITION | INGREDIENTS | SUM OF RANKS (DAY 4) | % GLA |
|---|---|---|---|
| 11 | Base Formula A + 8% Glycolic Acid | 52.0 | |
| 13 | Composition #11 + 0.5% Borage Seed Oil | 65.5 | 0.115 |
| 14 | Composition #11 + 1.0% Borage Seed Oil | 78.0* | 0.23 |

*Significantly less irritating than Composition #11.

It can be seen from the results in Table 4 that after four exposures, 8% glycolic acid (#11) was significantly more irritating than the same composition containing 1% Borage seed oil (#14). Upon addition of 0.5% Borage seed oil (#14), irritation was directionally less as was previously shown in Example 3.

EXAMPLE 5

A typical oil-in-water emulsion within the scope of the invention is as follows:

| chemical name | wt. % |
| --- | --- |
| propylene glycol | 1 |
| glycerin | 1 |
| hydroxyethylcellulose | 0.5 |
| magnesium aluminum silicate | 0.5 |
| imidazolidinyl urea | 0.5 |
| tetrasodium EDTA | 0.05 |
| petrolatum | 2 |
| isopropyl palmitate | 5 |
| dimethicone | 0.5 |
| cholesterol | 0.5 |
| cetyl alcohol | 0.5 |
| isostearic acid | 3 |
| retinyl palmitate | 0.1 |
| peg-40 stearate | 1 |
| peg-100 stearate | 1 |
| sorbitan stearate | 1 |
| borage seed oil | 0.5 |
| glycolic acid | 7 |
| ammonium hydroxide | to pH 4.0 |
| water DI | qs to 100% |

EXAMPLE 6

Another typical oil-in-water emulsion within the scope of the invention is as follows:

| chemical name | wt. % |
| --- | --- |
| propylene glycol | 1 |
| hydroxyethylcellulose | 0.5 |
| magnesium aluminum silicate | 0.5 |
| imidazolidinyl urea | 0.2 |
| petrolatum | 2 |
| isopropyl palmitate | 5 |
| dimethicone | 0.5 |
| cholesterol | 0.5 |
| stearic acid | 3 |
| isostearic acid | 1.5 |
| glycerol stearate | 1.5 |
| peg-40 stearate | 1 |
| peg-100 stearate | 1 |
| sorbitan stearate | 1 |
| cetyl alcohol | 0.5 |
| borage seed oil | 1 |
| glycolic acid | 10 |
| ammonium hydroxide | to pH 3.8 |
| water DI | qs to 100% |

EXAMPLE 7

A typical water-in-oil dispersion within the scope of the invention is as follows:

| chemical name | wt. % |
| --- | --- |
| isostearyl neopentanoate | 20 |
| peg-8 caprylic/capric glycerides | 16 |
| cetyl octanoate | 17 |
| polyglyceryl-6 dioleate | 15 |
| cyclomethicone | 20 |
| glyceryl isostearate | 0.5 |

-continued

| chemical name | wt. % |
| --- | --- |
| isostearic acid | 0.5 |
| ceramide III | 0.1 |
| ppg-5-cetheth-20 | 3 |
| L-lactic acid/potassium lactate | 6 |
| hydroxycaprylic acid | 0.1 |
| water DI | 1.3 |
| borage seed oil | 0.5 |

EXAMPLE 8

The following oil-in-water emulsion within the scope of the invention is prepared:

| chemical name | wt. % |
| --- | --- |
| glycerin | 1 |
| tetrasodium EDTA | 0.1 |
| cetyl alcohol | 1 |
| stearyl alcohol | 1 |
| mineral oil | 5 |
| dimethicone | 1 |
| cyclomethicone | 0.5 |
| dimethiconol | 0.2 |
| polyquaternium 37 | 2 |
| steareth-21 | 1 |
| steareth-2 | 0.5 |
| salicylic acid | 2 |
| borage seed oil | 0.5 |
| triethanolamine | to pH 3.0 |
| water DI | qs to 100% |

EXAMPLE 9

The following oil-in-water emulsion within the scope of the invention is prepared:

| chemical name | wt. % |
| --- | --- |
| xanthan gum | 0.2 |
| disodium EDTA | 0.1 |
| sodium PCA | 0.5 |
| diazodinyl urea | 0.3 |
| titanium dioxide | 1 |
| stearic acid | 3 |
| cyclomethicone | 0.3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6 |
| borage seed oil | 0.5 |
| glycolic acid | 3 |
| malic acid | 2 |
| lactic acid | 2 |
| green tea extract | 1 |
| triethanolamine | to pH 3.8 |
| water DI | qs to 100% |

EXAMPLE 10

The following oil-in-water emulsion within the scope of the invention is prepared:

| chemical name | wt. % |
|---|---|
| all-trans retinoic acid | 0.05 |
| light mineral oil | 10 |
| stearoxytrimethylsilane and stearyl alcohol | 5 |
| dimethicone | 2 |
| stearyl stearate | 10 |
| quaternium-15 | 3 |
| peg-22 dodecyl glycol copolymer | 1 |
| borage seed oil | 1 |
| sorbitol | 0.5 |
| methyl paraben | 0.2 |
| disodium EDTA | 0.1 |
| butylated hydroxytoluene | 0.1 |
| water DI | qs to 100% |

EXAMPLE 11

The following oil-in-water emulsion within the scope of the invention is prepared:

| chemical name | wt. % |
|---|---|
| squalane | 20 |
| macadamia oil | 5 |
| pentaerythritol tetraoctanoate | 15 |
| petrolatum | 5 |
| glyceryl stearate | 3 |
| tocopherol acetate | 0.5 |
| butylated hydroxytoluene | 0.05 |
| methyl paraben | 0.15 |
| propyl paraben | 0.15 |
| retinol | 0.1 |
| borage seed oil | 0.25 |
| sodium citrate | 1 |
| ascorbic acid | 1 |
| butylene glycol | 2 |
| glycerol | 2 |
| bentone clay | 0.2 |
| disodium EDTA | 0.05 |
| water DI | qs to 100% |

EXAMPLE 12

The following oil-in-water emulsion within the scope of the invention is prepared:

| chemical name | wt. % |
|---|---|
| glycerin | 1.5 |
| butylene glycol | 2.2 |
| disodium EDTA | 0.05 |
| methyl paraben | 0.1 |
| xanthan gum | 0.2 |
| magnesium aluminum silica | 0.3 |
| hydroxyethyl cellulose | 0.2 |
| glyceryl monohydroxystearate | 2 |
| stearyl alcohol | 1.5 |
| cholesterol | 0.5 |
| sorbitan stearate | 1 |
| peg-100 stearate | 2 |
| sodium stearyl lactylate | 0.4 |
| propyl paraben | 0.1 |
| borage seed oil | 4 |
| black currant seed oil | 5 |
| evening primerose oil | 3 |
| isostearyl palmitate | 18 |
| butylated hydroxystearate | 0.05 |
| retinol | 0.075 |
| retinyl palmitate | 0.06 |
| tocopherol acetate | 0.1 |
| alpha bisabolol | 0.2 |
| glycolic acid | 8 |
| potassium hydroxide | to pH 3.8 |
| water DI | qs to 100% |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A oil-in-water cosmetic emulsion comprising:

(i) a cosmetic benefit ingredient selected from the group consisting of an α-hydroxy acid, retinol, retinoic acid, retinal, $C_2$-$C_5$ retinyl ester and mixtures thereof;

(ii) borage seed oil in an amount effective to ameliorate the irritation to the skin induced by the cosmetic benefit ingredient; and (iii) from about 50% to about 99% of water.

2. The composition of claim 1 wherein the cosmetic benefit ingredient is a hydroxy acid, which is present in an amount of from 0.01 to 20% by weight of the composition.

3. The composition of claim 2 wherein the amount of the hydroxy acid is from 2 to 12% by weight of the composition.

4. The composition of claim 1 wherein the cosmetic benefit ingredient is a retinol or a retinyl ester, which is present in an amount of from 33 to 330,000 IU per gram of the composition.

5. The composition of claim 1 wherein the cosmetic benefit ingredient is selected from the group consisting of retinol, glycolic acid, lactic acid, and mixtures thereof.

6. The composition of claim 1 wherein borage seed oil is present in an amount of from about 0.05% to about 10%, by weight of the composition.

7. A method for reducing irritation induced by the topical application of an oil-in-water cosmetic emulsion containing an α-hydroxyacid or a retinoid, the method comprising topically applying borage seed oil in an amount effective to reduce irritation induced by the emulsion.

* * * * *